(12) United States Patent
Ueta

(10) Patent No.: US 6,842,240 B2
(45) Date of Patent: Jan. 11, 2005

(54) COLOR FILTER INSPECTION APPARATUS

(75) Inventor: Kunio Ueta, Kyoto (JP)

(73) Assignee: Dainippon Screen Mfg. Co., Ltd., Kyoto (JP)

( * ) Notice: Subject to any disclaimer, the term of this patent is extended or adjusted under 35 U.S.C. 154(b) by 0 days.

(21) Appl. No.: 10/372,949

(22) Filed: Feb. 26, 2003

(65) Prior Publication Data

US 2003/0184741 A1 Oct. 2, 2003

(30) Foreign Application Priority Data

Mar. 29, 2002 (JP) .................................... P2002-093562

(51) Int. Cl.[7] ............................................. G01N 21/00
(52) U.S. Cl. .................................................. 356/239.2
(58) Field of Search .......................... 356/239.1–239.3, 356/237.1–237.5; 430/7; 427/164, 553; 347/106, 107

(56) References Cited

U.S. PATENT DOCUMENTS

| | | | | |
|---|---|---|---|---|
| 5,400,135 A | * | 3/1995 | Maeda | 356/239.1 |
| 5,773,173 A | * | 6/1998 | Nakano et al. | 430/30 |
| 6,221,544 B1 | * | 4/2001 | Hayashi et al. | 430/7 |

FOREIGN PATENT DOCUMENTS

| | | | |
|---|---|---|---|
| JP | 7-12742 | | 1/1995 |
| JP | 7-270338 | * | 7/1995 |
| JP | 10-142101 | | 5/1998 |
| JP | 10-246705 | * | 10/1998 |
| JP | 11-64233 | * | 11/1999 |
| JP | 2000-337999 | * | 12/2000 |
| JP | 2001-141607 | * | 5/2001 |

* cited by examiner

*Primary Examiner*—Michael P. Stafira
(74) *Attorney, Agent, or Firm*—McDermott Will & Emery LLP

(57) ABSTRACT

In a color filter inspection apparatus (1), an image pickup part (13) for performing an image pickup of a color filter (9) which travels along guide rails (23) from above with a line sensor (130) and a fluorescence lamp (14) for irradiating the color filter (9) with an illumination light from below are provided and an optical filter (131) which transmits a light in a predetermined wavelength band is attached to the image pickup part (13). A transmission wavelength band of the optical filter (131) is a wavelength band in which the transmittance of one color component filter of the color filter (9) is high and transmittances of other color component filters are low. It is thereby possible to inspect unevenness in color of the color filter (9) with respect to one color component filter with high precision.

8 Claims, 6 Drawing Sheets

COLOR FILTER INSPECTION APPARATUS

BACKGROUND OF THE INVENTION

1. Field of the Invention

The present invention relates to a color filter inspection apparatus for inspecting unevenness in color of a color filter for a display.

2. Description of the Background Art

When a color filter for a display such as a flat panel display typified by a liquid crystal display is inspected singly, usually, the color filter is irradiated with an orange-colored light of a sodium-vapor lamp or a green light from a lamp called a green lamp. Then, unevenness (mura) in color of the color filter is inspected by visual check of transmission and reflection of the light.

It is very hard, however, to inspect the unevenness in color of the patterned color filter by visual check, and in some cases, the unevenness is not detected until a lighting check is performed after actually manufacturing a display panel.

SUMMARY OF THE INVENTION

The present invention is directed to a color filter inspection apparatus for inspecting unevenness in color of a color filter for a display, and it is an object of the present invention to inspect the unevenness in color of the color filter by transillumination with high precision.

According to the present invention, the color filter inspection apparatus comprises a supporter for supporting a color filter in which a transmittance of one color component filter in a specific wavelength band is higher than a sum of transmittances of other color component filters in the specific wavelength band, a light source for emitting a light to one main surface of the color filter, and an image pickup part located opposite to another main surface of said color filter, for acquiring a two-dimensional image of the color filter by receiving a light in the specific wavelength band from the color filter.

Using a specific wavelength band, the present invention makes it possible to inspect unevenness in color of the color filter with high precision.

Preferably, the transmittance of the one color component filter in the specific wavelength band is as high as or higher than the quadruple of the sum of transmittances of the other color component filters in the specific wavelength band.

According to a preferred embodiment of the present invention, the color filter inspection apparatus further comprises an optical filter provided between the light source and the image pickup part, for substantially removing lights in wavelength bands other than the specific wavelength band, and the light source is a discharge lamp. This allows an easy inspection with high precision.

According to another preferred embodiment of the present invention, the light source has a plurality of LEDs and it is therefore possible to simplify the apparatus and extend the lifetime of the light source.

More preferably, an image pickup direction of the image pickup part is inclined with respect to a normal of a main surface of the color filter supported by the supporter.

These and other objects, features, aspects and advantages of the present invention will become more apparent from the following detailed description of the present invention when taken in conjunction with the accompanying drawings.

DESCRIPTION OF THE PREFERRED EMBODIMENTS

Figure 1:
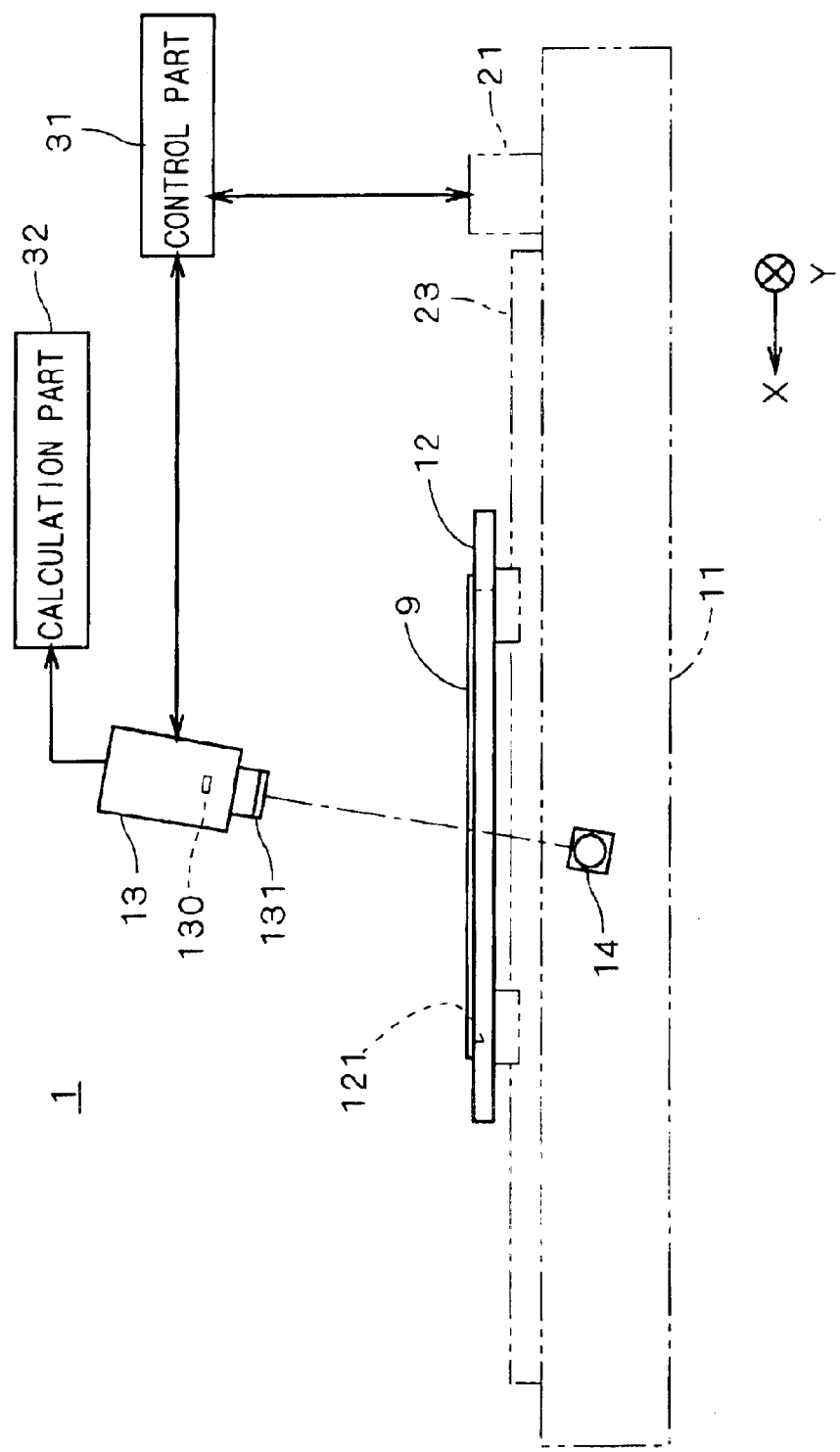
FIG. 1 is an elevation showing a constitution of a color filter inspection apparatus in accordance with a first preferred embodiment.
Figure 2:
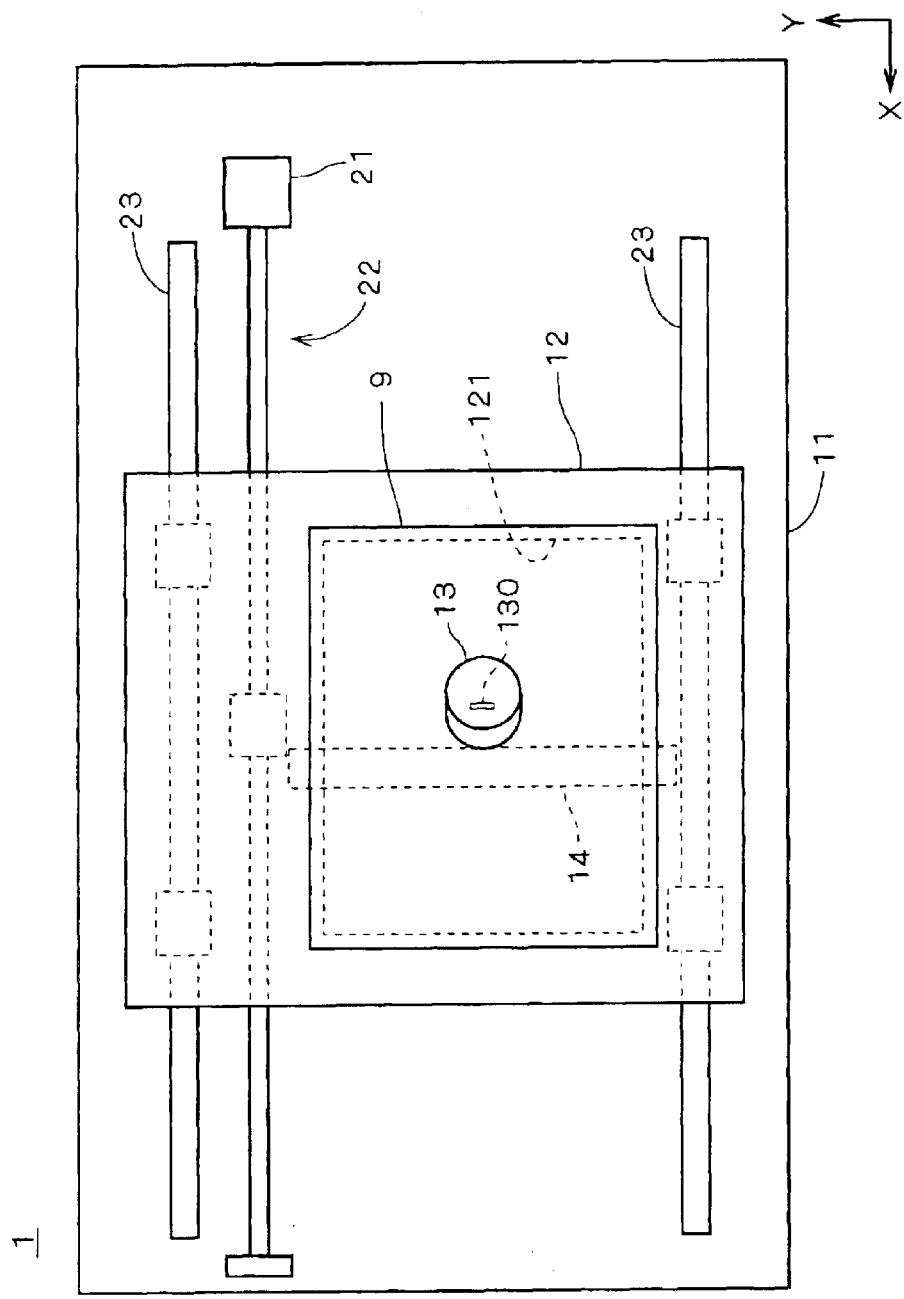
FIG. 2 is a plan view showing the constitution of the color filter inspection apparatus.

FIG. 1 is an elevation showing a constitution of a color filter inspection apparatus 1 in accordance with the first preferred embodiment of the present invention while FIG. 2 is a plan view thereof. In FIG. 1, for clear illustration, part of the constitution is indicated by phantom lines. The color filter inspection apparatus 1 serves to inspect unevenness in color of a color filter 9 used in a display such as a liquid crystal display, which is caused by variation in the amount of applied color resist or abnormality of some nozzles in a manufacturing process.

In the color filter inspection apparatus 1, a stage 12 having an opening 121 is provided on a base 11, being movable in the X direction, and the color filter 9 is supported on the opening 121 of the stage 12. An image pickup part 13 having a line sensor 130 is disposed above the stage 12 (i.e., located opposite to the upper surface of the color filter 9), and a fluorescence lamp 14 is disposed below the stage 12 (i.e., located opposite to the lower surface of the color filter 9). The image pickup part 13 performs an image pickup of a long area along the Y direction (a direction perpendicular to the paper) through an inside optical system. The fluorescence lamp 14 is disposed, facing towards the Y direction, correspondingly to an image pickup area, to emit an illumination light towards a lower main surface of the color filter 9.

On the base 11, as shown in FIG. 2, a ball screw mechanism 22 connected to a motor 21 and guide rails 23 for guiding the travel of the stage 12 are disposed, and the stage 12 is transferred along the guide rail 23 in the X direction by driving the motor 21. The color filter 9 is thereby transferred along the main surface. At a tip of the image pickup part 13, as shown in FIG. 1, an optical filter 131 which is a wavelength selection filter is provided.

The image pickup part 13 and the motor 21 are connected to a control part 31 (shown in FIG. 1). The control part 31 synchronizes the image pickup of the image pickup part 13 and the travel of the stage 12, to control acquisition of a two-dimensional image of the color filter to be performed by the image pickup part 13. An output of the image pickup part 13 is transmitted to an calculation part 32, where an inspection is performed on whether or not there is unevenness in color.

The image pickup and the calculation are performed on each of the three color component filters of R (Red), G (Green) and B (Blue) (i.e., color resists) of the color filter 9, and at this time, the optical filters 131 corresponding to these colors are sequentially attached to the image pickup part 13.

As shown in FIG. 1, the image pickup direction of the image pickup part 13 (the direction of an optical axis of the optical system) is inclined with respect to a normal of the main surface of the color filter 9 supported by the stage 12. The angle of inclination is, e.g., about 10 degrees. This prevents the image pickup part 13 (especially, the tip of the optical system) from being reflected in the color filter 9 and imaged, to allow acquisition of a proper image.

Figure 3:
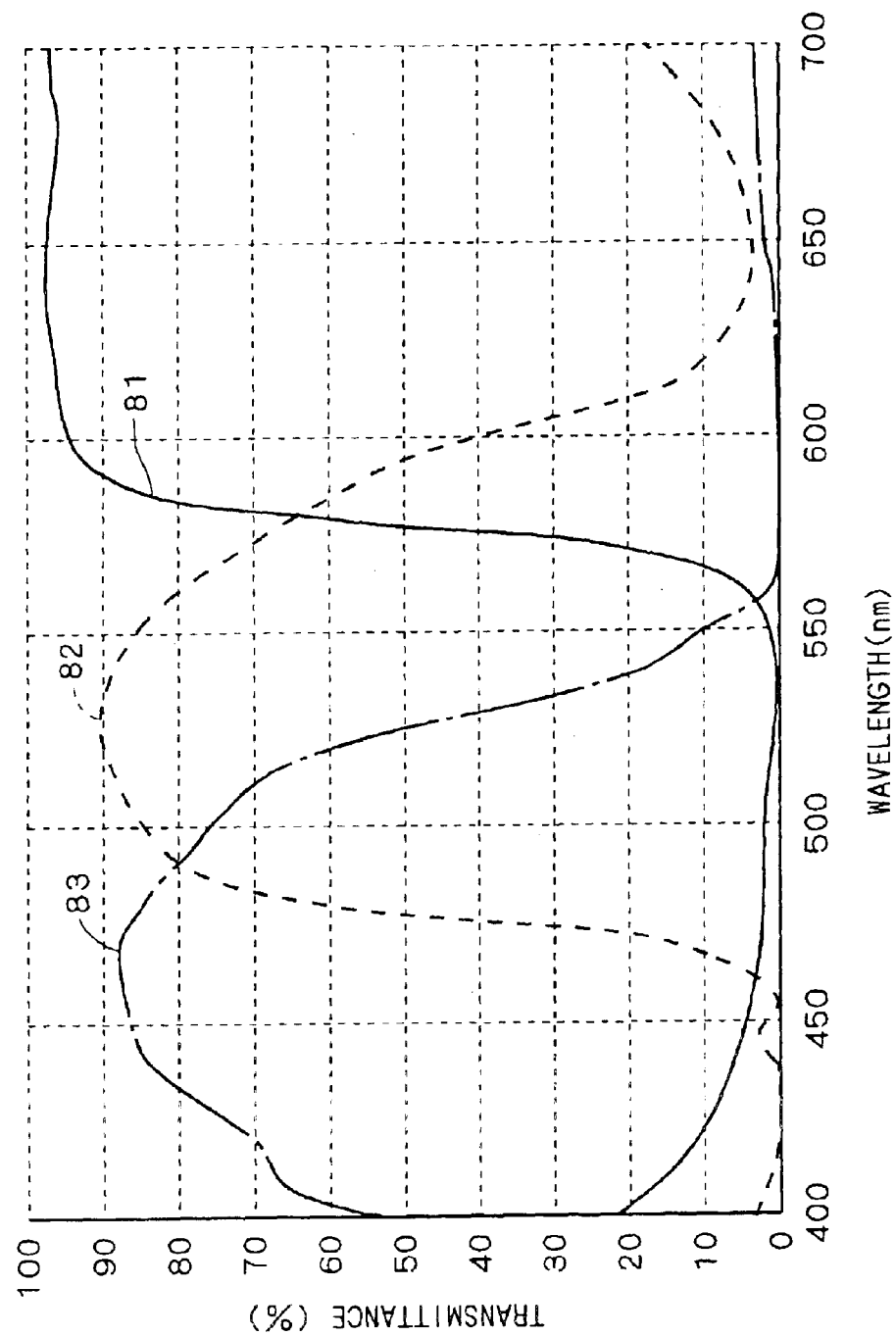
FIG. 3 is a graph showing spectral transmittances of color component filters.

Next, the characteristics of the optical filter 131 will be discussed. A curve 81 of FIG. 3 indicates the spectral transmittance of the color component filter of R (i.e., the color resist of R) and curves 82 and 83 indicate the spectral transmittances of the color component filters of G and B, respectively. As shown in FIG. 3, the spectral transmittances of R, G and B are not fully separated with respect to the wavelength. Therefore, a high-precision inspection can not be achieved when a light having a wide wavelength band is used.

Figure 4:
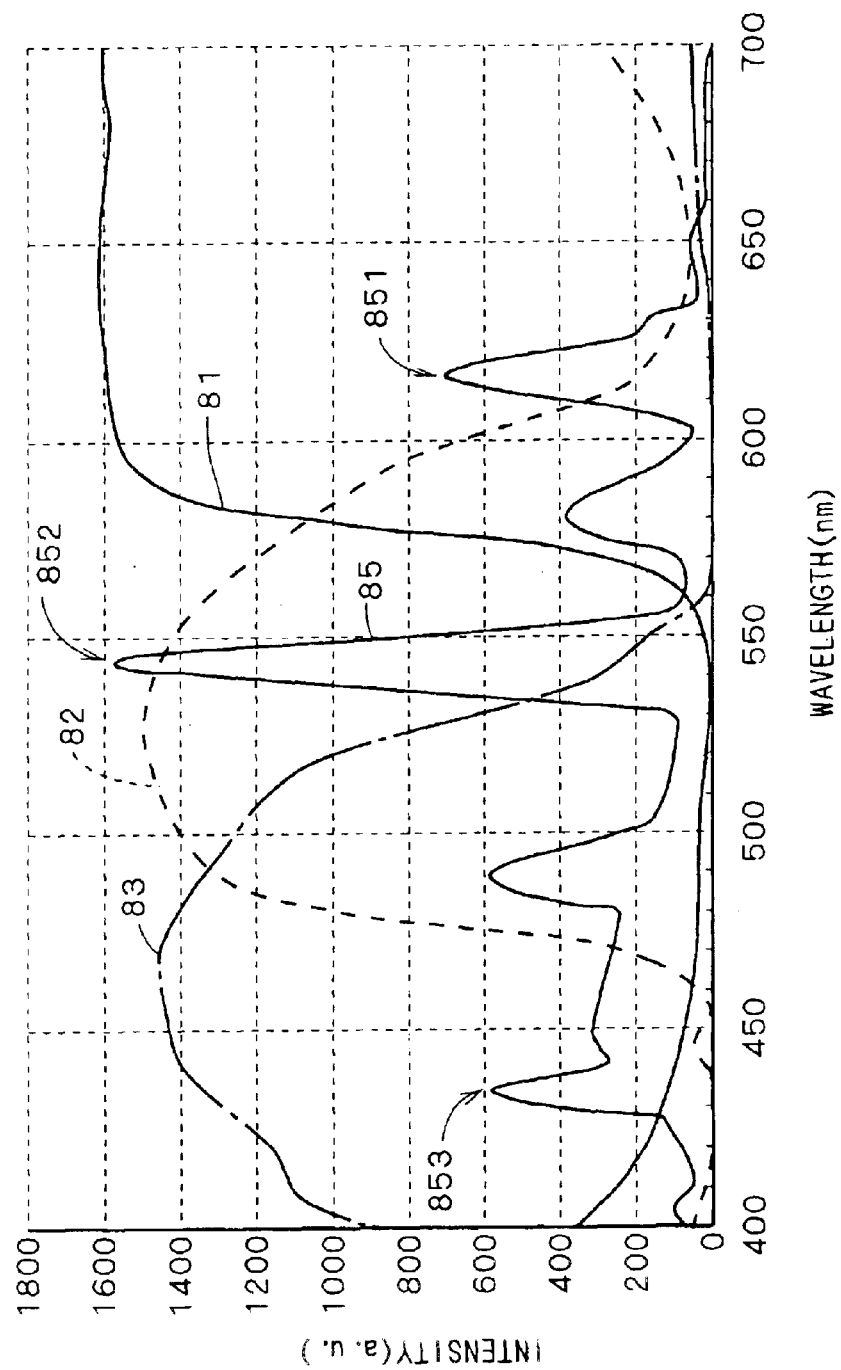
FIG. 4 is a graph showing spectral intensity of a light emitted from a fluorescence lamp.

FIG. 4 is a graph showing spectral intensity (indicated by a curve 85) of a light emitted from the fluorescence lamp 14 having the same spectral characteristics as the light source of the liquid crystal display has, and the three curves 81 to 83 of FIG. 3 are also shown in this figure regardless of the scale on the vertical axis for convenience of explanation. As shown in FIG. 4, the light emitted from the discharge lamp such as the fluorescence lamp 14 has an emission line spectrum and wavelength bands having high intensity are limited. Then, in the color filter inspection apparatus 1, when an inspection is performed on the R component (the color component filter of R) of the color filter 9, a filter which transmits a light having a wavelength of 600 nm or more is used as the optical filter 131 and only the light in a wavelength band with a peak 851 in FIG. 4 is used for the inspection. It is thereby possible to properly inspect unevenness of the R component without effects of the transmittances of the G component and the B component of the color filter.

When an inspection is performed on the G component, only the light in a wavelength band near a peak 852 is used for the inspection. Specifically, a filter which transmits a light in the wavelength band ranging from 500–530 nm to 550–570 nm is used as the optical filter 131. When an inspection is performed on the B component, only the light in a wavelength band near a peak 853 is used for the inspection, and specifically a filter which transmits a light in the wavelength band of 440–480 nm or less is used as the optical filter 131.

As discussed above, in the color filter inspection apparatus 1, the image pickup part 13 receives the light in the wavelength band in which the transmittance of one color component filter is high and the transmittance of any other color component filter is low, to acquire a two-dimensional image which corresponds to the transmittance distribution of a specific color component filter of the color filter 9. As a result, it is possible to inspect unevenness of each color filter with high precision and obtain a useful information for the manufacturing process.

Further, using the discharge lamp such as the fluorescence lamp 14 (among other examples are a xenon arc lamp and a metal halide lamp) as the light source, the color filter inspection apparatus 1 allows an easy high-precision inspection with the emission line spectrum of the light from the discharge lamp even if the optical filter 131 does not precisely transmit only the light in the specific wavelength band. When an inspection is performed on the filters of R component or B component, particularly, a high-precision inspection can be achieved only by providing the optical filter 131 (e.g., colored glass filter) which transmits only a light having a wavelength longer or shorter than a predetermined wavelength in consideration of the wavelength band of the emission line spectrum.

With the image pickup part 13 having the line sensor 130, it is possible to suppress bloating of the optical system in the image pickup part 13 and achieve an easy inspection even if the large-sized color filter 9 is inspected.

As shown in FIG. 3, there is no case, generally, where the spectral transmittances of two color component filters are both zero. Therefore, even if a light in any wavelength band is used for the inspection of a filter of one color component (hereinafter, referred to as "specific color component"), it is impossible to completely avoid the effect of unevenness of other color component filters. When the transmittance of the specific color component filter is higher than the sum of transmittances of other color component filters, the effect of the specific color component filter becomes predominant in the acquired image and therefore the inspection can be properly performed.

For higher-precision inspection, it is preferable that the transmittance of the specific color component filter should be as high as or higher than the quadruple of the sum of transmittances of other color component filters.

Figure 5:
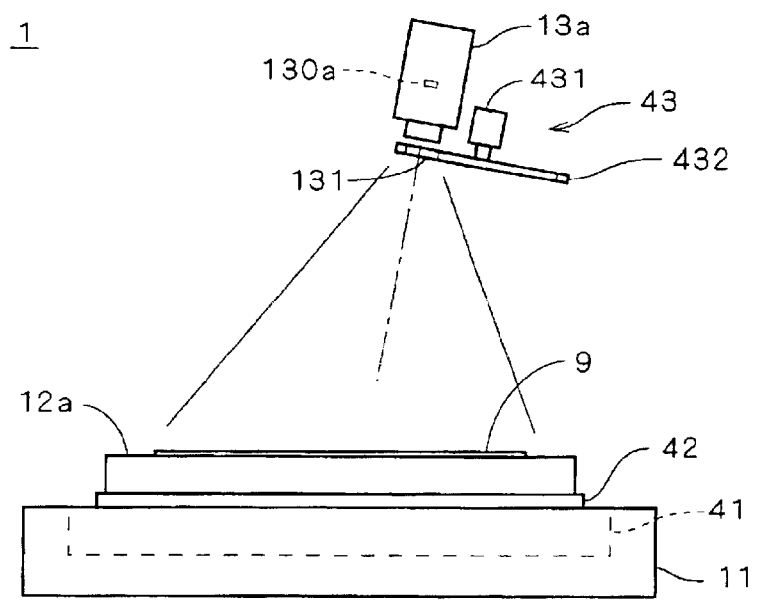
FIG. 5 is an elevation showing a color filter inspection apparatus in accordance with a second preferred embodiment.
Figure 6:
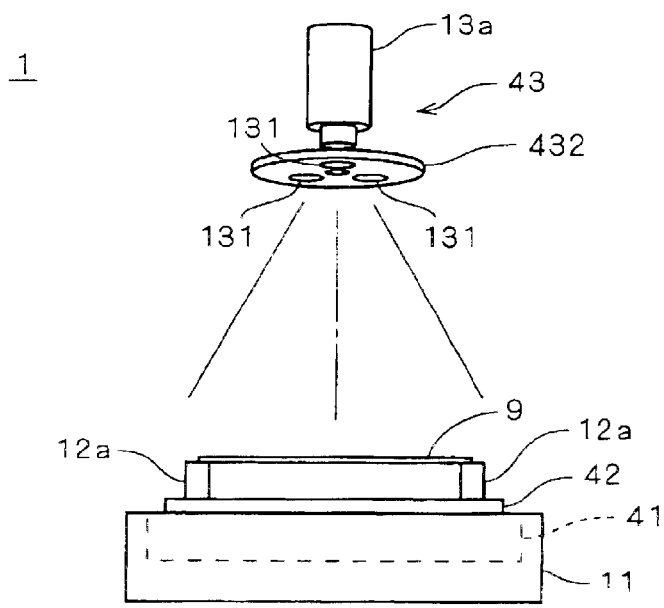
FIG. 6 is a left side view of the color filter inspection apparatus.

FIG. 5 is an elevation showing a color filter inspection apparatus 1 in accordance with the second preferred embodiment while FIG. 6 is a left side view thereof. In the color filter inspection apparatus 1 of the second preferred embodiment, a light box 41 is provided in the base 11 and a photodiffusion panel 42 is attached on the light box 41. On the photodiffusion panel 42, two supporting guides 12a are disposed and the color filter 9 is placed on the supporting guides 12a.

An image pickup part 13a has a two-dimensional image pickup device 130a and acquires a two-dimensional image of the color filter 9 without transferring the color filter 9. Between the color filter 9 and the image pickup part 13a, a switching mechanism 43 is disposed to switch the optical filter 131 to one for each color component. The switching mechanism 43 rotates a disk 432 to which the optical filters 131 are attached with a motor 431 (see FIG. 5), to sequentially position the optical filters 131 ahead of the image pickup part 13a. Like in the first preferred embodiment, the image pickup direction of the image pickup part 13a is inclined with respect to the direction of a normal of the color filter 9 to prevent unnecessary reflection.

As the light source in the light box 41, a fluorescence lamp may be used like in the first preferred embodiment or a light source having a filament may be used. When a light having no emission line spectrum is emitted, the optical filters 131 in consideration of the characteristics of the color components shown in FIG. 3 are prepared. For example, three optical filters 131 which have wavelength ranges centering on 620 nm, 545 nm and 440 nm, respectively, and a half band width of about 10 nm are attached to the disk 432 for the R component, the G component and the B component.

It is natural that the characteristics of the optical filter 131 may be changed as appropriate in accordance with the sensitivity characteristics of the image pickup part 13a, the spectral transmittance of each color component filter, the spectral intensity of the light source or the like, and if it is possible to substantially remove lights other than the light in the specific wavelength band in accordance with these characteristics, the optical filter 131 does not strictly have to transmit only the light in the specific wavelength band.

As discussed above, the color filter inspection apparatus 1 can also use the two-dimensional image pickup device 130a, and in this case, there is no need of the mechanism for transferring the color filter 9.

Figure 7:
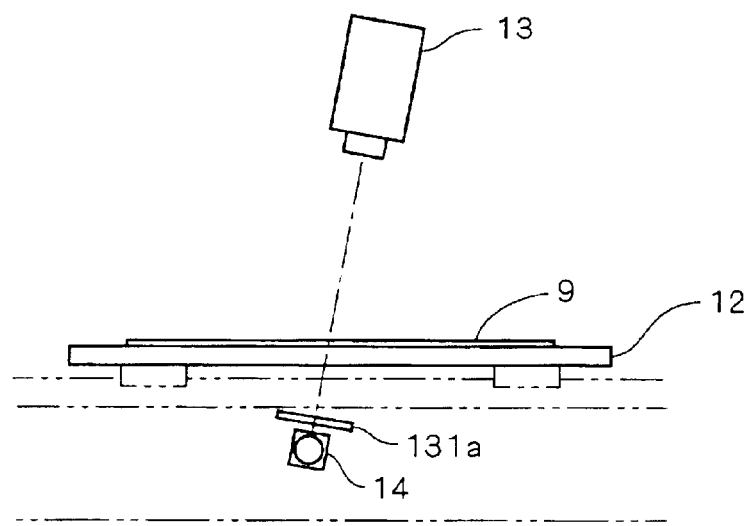
FIG. 7 is a view showing part of a constitution of another color filter inspection apparatus.

FIG. 7 is a view showing part of a constitution of another color filter inspection apparatus. The color filter inspection apparatus of FIG. 7 has the same constitution as that of the first preferred embodiment except that an optical filter 131a is disposed between the fluorescence lamp 14 and the color filter 9. Thus, the optical filter may be arbitrarily disposed between the image pickup part and the light source.

Figure 8:
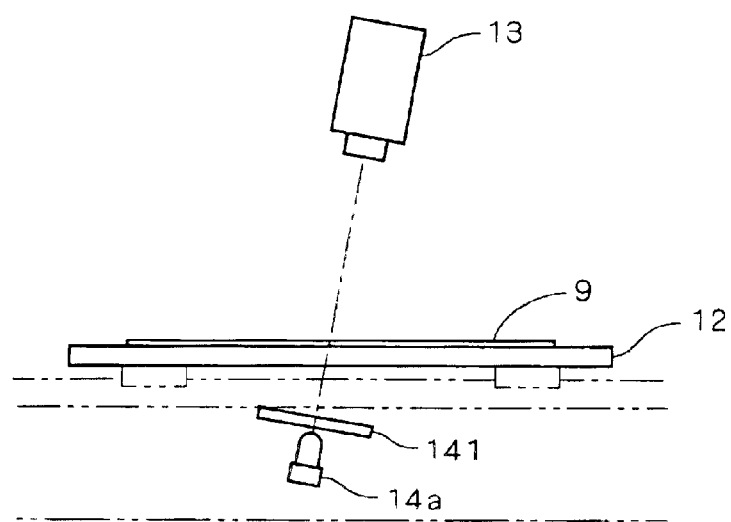
FIG. 8 is a view showing part of a constitution of still another color filter inspection apparatus.

FIG. 8 is a view showing part of a constitution of still another color filter inspection apparatus. The color filter inspection apparatus of FIG. 8 uses an LED array 14a consisting of a plurality of LEDs (light emitting diodes) arranged in a direction perpendicular to the paper as a light source and no optical filter 131 is provided, unlike in the first preferred embodiment. Between the LED array 14a and the color filter 9 provided is a photodiffusion panel 141 for giving uniform linear illumination to the color filter 9.

When the LEDs are used as the light source, since the illumination light has a single emission line spectrum, there is no need of the optical filter 131 and the apparatus constitution is thereby simplified. Further, the lifetime of the light source can be extended. Three kinds of LED arrays 14a are prepared for emitting lights in accordance with the respective characteristics of the color component filters and sequentially changed.

Though the preferred embodiments of the present invention have been discussed above, the present invention is not limited to the above-discussed preferred embodiments, but allows various variations.

For example, as a light source for emitting linear illumination perpendicular to a scanning direction of the line sensor 130 (the X direction of FIGS. 1 and 2), combination of an optical fiber array or a quartz rod and a light source may be used.

If the color filter 9 is large and hard to support only at its limb, a beam for supporting the center portion of the color filter 9 may be provided in the opening 121 of the stage 12 shown in FIG. 2 or between the two supporting guides 12a shown in FIG. 6.

When the image pickup part 13 having the line sensor 130 is used, though the inspection of unevenness in color is repeated for the three color components while an operator changes the optical filters 131 in the above preferred embodiment, three sets of the image pickup part 13 having the line sensor 130, the fluorescence lamp 14 (light source) and the optical filter 131 (or three combinations of the image pickup part 13 and the LED arrays 14a) may be provided for the three color components, respectively. It is thereby possible to inspect three color component filters with only one scan of the color filter 9.

Only if the travel of the color filter 9 is achieved relatively to the image pickup part 13 having the line sensor 130, the image pickup part 13 may be transferred relatively to the color filter 9.

While the invention has been shown and described in detail, the foregoing description is in all aspects illustrative and not restrictive. It is therefore understood that numerous modifications and variations can be devised without departing from the scope of the invention.

What is claimed is:

1. A color filter inspection apparatus for inspecting unevenness in color of a color filter for a display, comprising:

a supporter for supporting said color filter in which a transmittance of one color component filter in a specific wavelength band is higher than the sum of transmittances of other color component filters in said specific wavelength band;

a light source for emitting a light to one main surface of said color filter; and an image pickup part located opposite to another main surface of said color filter, for acquiring a two-dimensional image of said color filter by receiving light in said specific wavelength band from said color filter.

2. The color filter inspection apparatus according to claim 1, wherein said transmittance of said one color component filter in said specific wavelength band is as high as or higher than a quadruple of said sum of transmittances of said other color component filters in said specific wavelength band.

3. The color filter inspection apparatus according to claim 1, further comprising an optical filter provided between said light source and said image pickup part, for substantially removing light in wavelength bands other than said specific wavelength band.

4. The color filter inspection apparatus according to claim 1, further comprising an optical filter between said light source and said image pickup part, wherein said light source is a discharge lamp.

5. The color filter inspection apparatus according to claim 4, wherein said optical filter transmits only light having a wavelength longer or shorter than a predetermined wavelength.

6. The color filter inspection apparatus according to claim 1, wherein said light source has a plurality of LEDs.

7. The color filter inspection apparatus according to claim 1, wherein an image pickup direction of said image pickup part is inclined with respect to a normal of a main surface of said color filter supported by said supporter.

8. The color filter inspection apparatus according to claim 1, further comprising a transfer mechanism for transferring said supporter relatively along a main surface of said color filter, wherein said image pickup part has a line sensor for performing an image pickup in synchronization with travel of said supporter.

* * * * *